US010761058B2

(12) United States Patent
Chang et al.

(10) Patent No.: US 10,761,058 B2
(45) Date of Patent: Sep. 1, 2020

(54) NANOSTRUCTURES TO CONTROL DNA STRAND ORIENTATION AND POSITION LOCATION FOR TRANSVERSE DNA SEQUENCING

(71) Applicant: SEAGATE TECHNOLOGY LLC, Cupertino, CA (US)

(72) Inventors: Thomas Young Chang, Menlo Park, CA (US); David S. Kuo, Palo Alto, CA (US); Kim Yang Lee, Fremont, CA (US); Koichi Wago, Sunnyvale, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 55 days.

(21) Appl. No.: 15/886,608

(22) Filed: Feb. 1, 2018

(65) Prior Publication Data

US 2018/0246057 A1 Aug. 30, 2018

Related U.S. Application Data

(60) Provisional application No. 62/453,346, filed on Feb. 1, 2017.

(51) Int. Cl.
*G01N 27/447* (2006.01)
*B01L 3/00* (2006.01)
(Continued)

(52) U.S. Cl.
CPC .. *G01N 27/44791* (2013.01); *B01L 3/502761* (2013.01); *B82Y 15/00* (2013.01);
(Continued)

(58) Field of Classification Search
CPC ....... G01N 27/44791; G01N 33/48721; C12Q 1/6869; C12Q 2565/631; C12Q 2563/116;
(Continued)

(56) References Cited

U.S. PATENT DOCUMENTS 5,007,984 A 4/1991 Tsutsumi et al.
5,071,714 A 12/1991 Rodbell et al.
(Continued)

FOREIGN PATENT DOCUMENTS

WO WO-2015170782 A1 * 11/2015 .......... C12Q 1/6806

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.

(Continued)

*Primary Examiner* — Joseph G. Dauner
(74) *Attorney, Agent, or Firm* — Holzer Patel Drennan

(57) ABSTRACT

A DNA sequencing device, and related method, which include an electrode and a plurality of spaced apart alignment structures. The electrode defines an electrode gap, the electrode being operable to detect a change in tunneling current as a DNA strand passes through the electrode gap. The plurality of spaced apart alignment structures are arranged to position nucleotides of the DNA strand in a predetermined orientation as the DNA strand passes through the electrode gap.

11 Claims, 13 Drawing Sheets

(51) Int. Cl.
*G01N 33/487* (2006.01)
*C12Q 1/6869* (2018.01)
*B82Y 15/00* (2011.01)
*B82Y 30/00* (2011.01)

(52) U.S. Cl.
CPC ..... *C12Q 1/6869* (2013.01); *G01N 33/48721* (2013.01); *B01L 2200/0663* (2013.01); *B01L 2300/0645* (2013.01); *B01L 2300/0896* (2013.01); *B82Y 30/00* (2013.01); *C12Q 2565/631* (2013.01)

(58) Field of Classification Search
CPC ...... C12Q 1/6874; B82Y 15/00; B82Y 30/00; B01L 3/502761; B01L 2200/0663; B01L 2300/0645; B01L 2300/0896
See application file for complete search history.

(56) References Cited

U.S. PATENT DOCUMENTS

| | | | |
|---|---|---|---|
| 5,127,989 | A | 7/1992 | Haraguchi et al. |
| 6,627,067 | B1 | 9/2003 | Branton et al. |
| 7,582,490 | B2 | 9/2009 | Golovchenko et al. |
| 8,105,471 | B1 | 1/2012 | Han et al. |
| 9,410,923 | B2 | 8/2016 | Sauer et al. |
| 10,247,700 | B2 | 4/2019 | Hu et al. |
| 10,466,228 | B2 | 11/2019 | Ikeda et al. |
| 2002/0039737 | A1 | 4/2002 | Chan et al. |
| 2002/0081744 | A1* | 6/2002 | Chan ....................... B01F 5/061 436/164 |
| 2010/0188109 | A1 | 7/2010 | Edel |
| 2010/0267158 | A1 | 10/2010 | Chou et al. |
| 2011/0174629 | A1 | 7/2011 | Bouchet et al. |
| 2013/0334047 | A1 | 12/2013 | Jeong et al. |
| 2014/0151228 | A1 | 6/2014 | Royyuru et al. |
| 2014/0312002 | A1 | 10/2014 | Peng |
| 2016/0153105 | A1 | 6/2016 | Gumbercht |
| 2016/0319342 | A1 | 11/2016 | Kawai |
| 2017/0144158 | A1 | 5/2017 | Taniguchi |
| 2017/0146510 | A1 | 5/2017 | Ikeda et al. |
| 2017/0253479 | A1 | 9/2017 | Nikoobakht, IV |

OTHER PUBLICATIONS

Feng, Yanxiao, et al., "Nanopore-based Fourth-generation DNA Sequencing Technology," Genomics Proteomics Bioinformatics, 13 (2015), pp. 4-16.
Ivanov, A.P., et al., "DNA Tunneling Detector Embedded in a Nanopore," Nano Letters, 2011, 11, pp. 279-285.
Ke, Rongqin, et al., "Fourth Generation of Next-Generation Sequencing Technologies: Promise and Consequences," Human Mutation, vol. 37, No. 12, 2016, pp. 1363-1367.
Kulski, Jerzy K., "Next-Generation Sequencing—An Overview of the History, Tools, and 'Omic' Applications," http://dx.doi.org/10.5772/61964, 59 pages, published Jan. 14, 2016.
Duan et al., "Review article: Fabrication of nanofluidic devices," Biomicrofluidics 7, 026501 (2013).

* cited by examiner

NANOSTRUCTURES TO CONTROL DNA STRAND ORIENTATION AND POSITION LOCATION FOR TRANSVERSE DNA SEQUENCING

RELATED APPLICATIONS

This application claims the benefit of the filing date of U.S. Provisional Application No. 62/453,346, filed on 1 Feb. 2017, and entitled NANOSTRUCTURES TO CONTROL DNA STRAND ORIENTATION AND POSITION LOCATION FOR TRANSVERSE DNA SEQUENCING, the disclosure of which is incorporated in its entirety by this reference.

SUMMARY

One aspect of the present disclosure relates to a DNA sequencing device that includes an electrode and a plurality of spaced apart alignment structures. The electrode defines an electrode gap, the electrode being operable to detect a change in tunneling current as a DNA strand passes through the electrode gap. The plurality of spaced apart alignment structures are arranged to position nucleotides of the DNA strand in a predetermined orientation as the DNA strand passes through the electrode gap.

The DNA sequencing device may further include a nanochannel, the electrode gap being positioned in the nanochannel. At least some of the alignment structures may be positioned in the nanochannel. At least some of the alignment structures may be positioned outside of the nanochannel. The alignment structures may be arranged in at least one of a plurality of rows and a plurality of columns, and the alignment structures of one row or column may be offset from the alignment structures of an adjacent row or column. At least some of the alignment structures may have one of a hemispherical shape, a circular cross-sectional shape, and a rectangular cross-sectional shape. The electrode may include first and second electrode members, which are spaced apart to define the electrode gap, the electrode gap being in the range of about 0.3 nm to about 2 nm. The DNA sequencing device may include at least one additional electrode, each additional electrode defining an additional electrode gap. The electrode gap may be positioned in an open space between at least two of the alignment structures. The electrode gap may be positioned overlapping at least one of the alignment structures. The DNA sequencing device may include a tapered channel entry structure positioned at an entrance end of the nanochannel, which permits only a single DNA strand at a time to pass into the nanochannel.

Another aspect of the present disclosure relates to a method of forming a DNA sequencing device. The method includes forming a plurality of spaced apart alignment structures on a substrate, and positioning an electrode downstream of at least some of the plurality of alignment structures, the electrode defining an electrode gap. The alignment structures may be arranged relative to each other and the electrode gap so that DNA strands passing between the alignment structures are directed through the electrode gap at a predetermined orientation.

Forming the plurality of alignment structures may include arranging at least some of the plurality of alignment structures in rows, the alignment structures of one row being offset from the alignment structures in an adjacent row. At least some of the alignment structures may be positioned downstream of the electrode gap. The method may include depositing a channel layer on the substrate, forming a nanochannel in the channel layer, and positioning at least some of the alignment structures inside the nanochannel. The method may include depositing a channel layer on the substrate, forming a nanochannel in the channel layer, and positioning at least some of the alignment structures outside of the nanochannel.

Another aspect of the present disclosure relates to a method of sequencing DNA. The method includes providing a DNA sequencing device having an electrode and a plurality of alignment structures, the electrode defining an electrode gap, orienting a DNA strand with the plurality of alignment structures in a predetermined orientation relative to the electrode gap, passing the DNA strand through the electrode gap in the predetermined orientation, detecting a tunneling current as individual nucleotides of the DNA strand pass through the electrode gap, and sequencing the DNA strand using the detected tunneling current.

The DNA sequencing device may include a nanochannel, and the electrode gap and at least some of the alignment structures may be positioned in the nanochannel. The plurality of alignment structures may be arranged in rows, the alignment structures of one row may be offset from the alignment structures in an adjacent row, at least some of the alignment structures may be positioned upstream of the electrode, and at least some of the alignment structures may be positioned downstream of the electrode. The electrode may include first and second electrodes, which are spaced apart to define the electrode gap, the electrode gap being in the range of about 0.3 nm to about 2 nm.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Despite considerable efforts, DNA sequencing today still suffers from high costs and low speeds. To address all these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, and methods for creating such a device, have not been discovered. Conventional MEMS and nanofabrication methods are inadequate for creating the required structure.

Figure 1C:
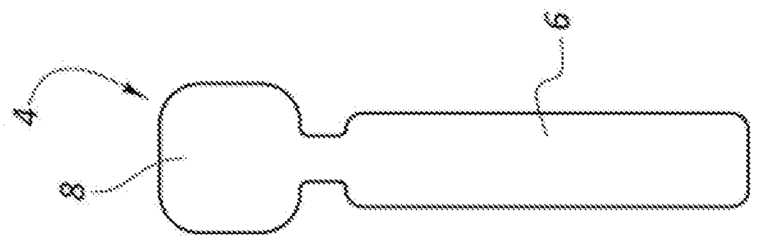
FIGS. 1B and 1C show schematic front and side views of a single nucleotide of a DNA strand.
Figure 1B:
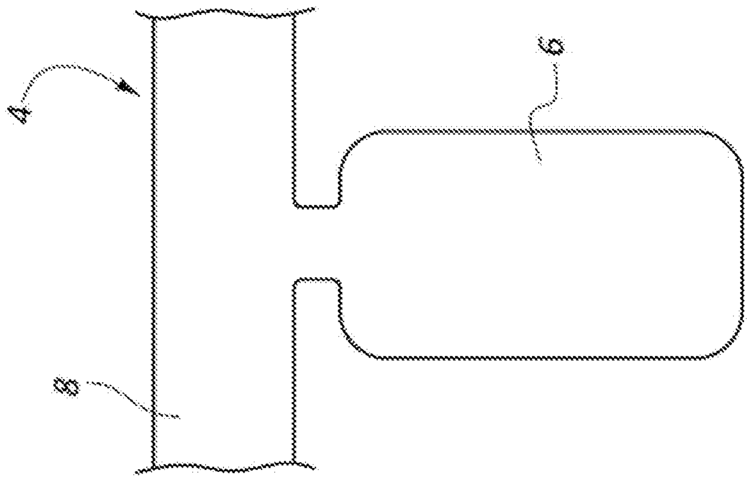
Figure 1A:
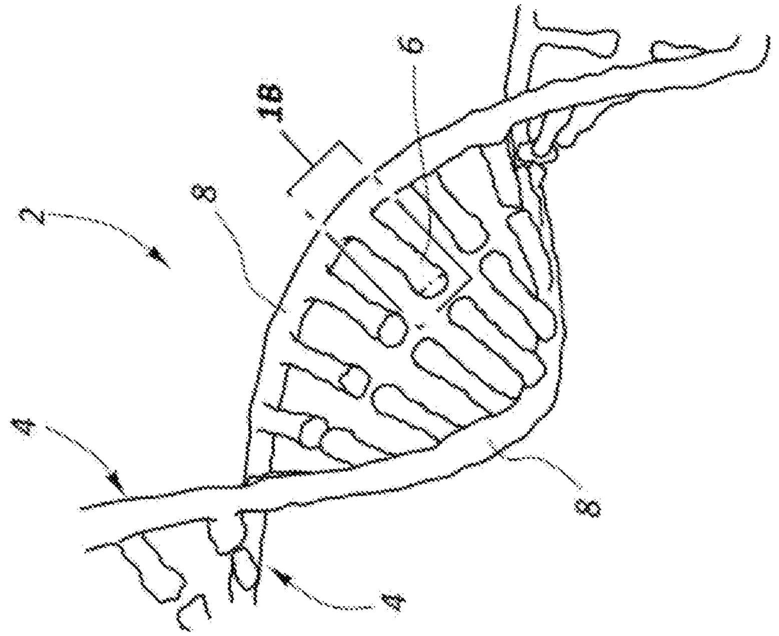
FIG. 1A shows a DNA double helix structure.
Figure 2:
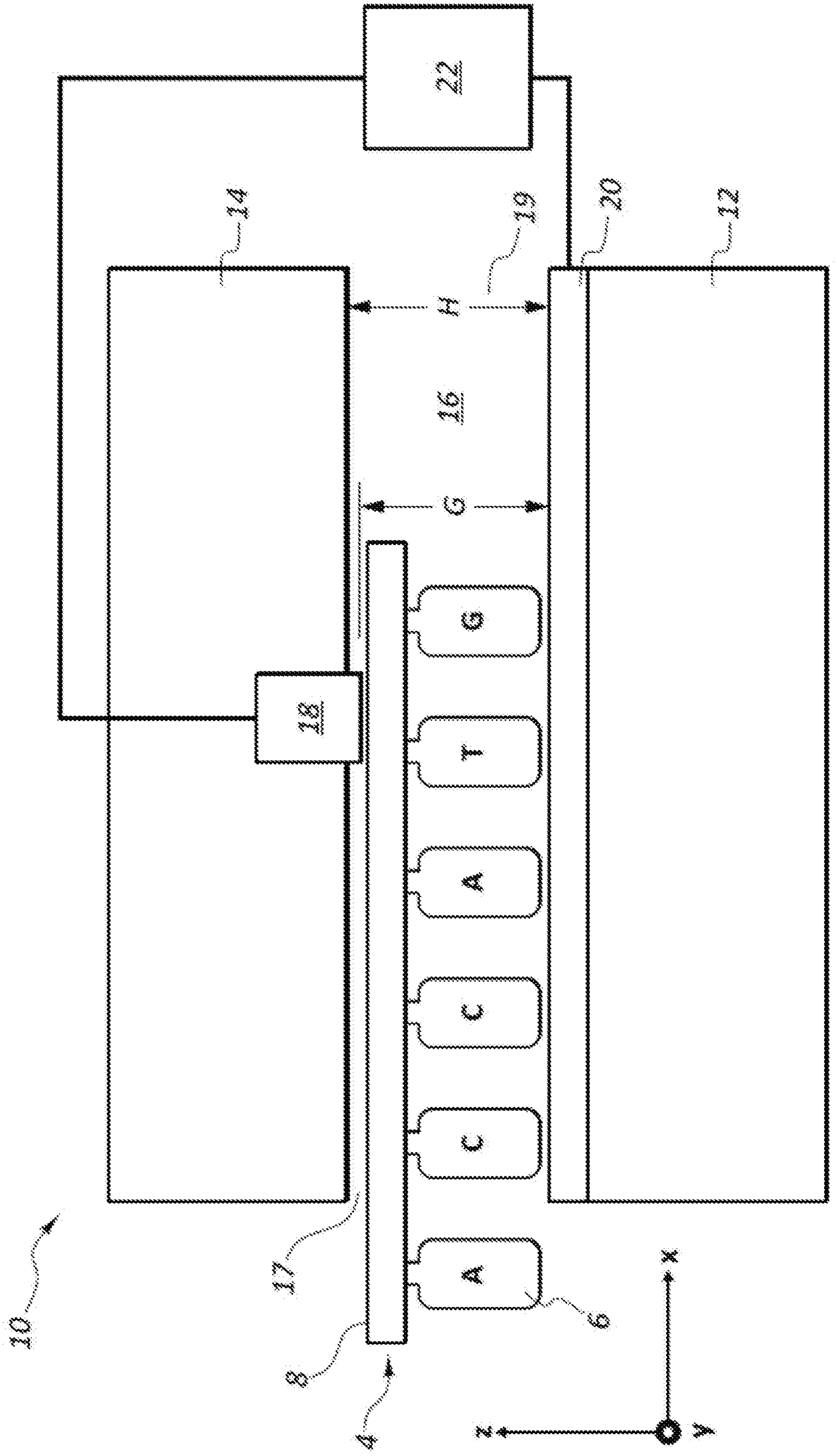
FIG. 2 shows a schematic side view of an example DNA sequencing device in accordance with the present disclosure.

In the DNA transverse sequencing process, a single DNA strand 4 (see FIGS. 1A-1C) taken from a DNA double helix 2 (see FIG. 1A) moves past an electrode as illustrated in FIG. 2. FIG. 2 shows a single DNA strand 4 with its backbone 8 oriented along an X axis, with individual nucleotides 6 oriented along the Z axis. This arrangement for the DNA strand 4 may be an ideal orientation of individual nucleotides 6 with respect to a pair of electrode members 18, 20 (generally referred to as an electrode or electrode pair) to maximize the tunneling current differentiation of the nucleotides. However, in an actual three dimensional (3D) channel, the nucleotides 6 may have many different orientations relative to the electrode members 18, 20 within the Y-Z plane, thus affecting the tunneling current signal and potentially reducing the ability to differentiate the nucleotides. The DNA sequencing devices of the present disclosure provide a more consistent orientation and position of the nucleotides 6 as they pass the electrode members 18, 20 in order to obtain the maximum signal to noise ratio (SNR) and differentiation of the individual nucleotides 6.

The present disclosure generally relates to DNA sequencing, and more particularly relates to DNA sequencing devices having nanochannels and nanoelectrodes, and related methods of fabricating such devices. The present disclosure may also relate to DNA sequencing using such devices. More particularly, the present disclosure relates to devices, systems and methods that require the DNA strand to pass through the probe in a consistent orientation. Providing a consistent, repeatable orientation for each DNA strand along that passes the electrode, and potentially an entire length of the DNA strand as it passes the electrode, makes nucleotide discrimination via measurement of the tunneling current much more practical and reliable.

Referring again to FIG. 2, a DNA sequencing device 10 is shown schematically in a side cross-sectional view. The DNA sequencing device 10 includes a substrate 12, an upper layer 14, a nanochannel 16, first and second electrode members 18, 20, and a controller or pre-amp 22. The nanochannel 16 has inlets and outlet ends 17, 19 and a height H. A space between the electrode members 18, 20 defines an electrode gap G. The nanochannel 16 is sized to receive a DNA strand 4 at the inlet end 17. The DNA strand 4, which includes a backbone 8 and a plurality of nucleotides 6 spaced along the length of the backbone 8, passes through the nanochannel 16 and between the electrode members 18, 20. The electrode members 18, 20 detect a change in tunneling current via the controller 22 as each of the nucleotides 6 passes through the gap G. The ability for the DNA sequencing device 10 to accurately and consistently detect the tunneling current for each of the nucleotides 6 is dependent at least in part on the orientation of the DNA strand 4 as it passes through the gap G. Providing a consistent orientation for the nucleotides 6 as they pass through the gap G can provide improved consistency and accuracy for the tunneling current measurement. Further, orienting the DNA strand 4 in such a way that the nucleotide 6 are aligned in the orientation shown in FIG. 2 (e.g., the length dimensions of the nucleotide 6 is aligned with the direction between the first and second electrode members 18, 20) may help enhance the signal to noise ratio (SNR) associated with the tunneling current measurement. Improving the signal to noise ratio (SNR) may improve the accuracy of detecting the particular nucleotide type (A,T,C,G) that is passing between the first and second electrode members 18, 20 at any given moment.

In other embodiments, it may be advantageous to orient the DNA strand at other rotated angles relative to the Z axis (e.g., the direction between the electrode members 18, 20) in order to maximize the signal to noise ratio and/or provide other advantages for detecting and/or distinguishing between the various nucleotides of a given DNA strand. The embodiments of the present disclosure described herein may assist in aligning the DNA strand 4 in a particular orientation relative to the nanochannel 16 and/or first and second electrode members 18, 20 as the DNA strand 4 passes through the gap G. For example, in some embodiments, one or more alignment structures is positioned in the nanochannel 16 to assist in orienting the DNA strand 4 such that the nucleotides 6 are arranged at a particular rotated position within the YZ plane, are positioned at a given location within the nanochannel 16, or other positional considerations. In other embodiments, one or more alignment structures may be positioned before or after of the electrode members 18, 20. In other embodiments, one or more alignment structures is positioned outside of the nanochannel 16 at a location before or after the nanochannel 16. In still further embodiments, the electrode members are positioned outside of the nanochannel, the nanochannel is used to restrict passage of a single DNA strand through the DNA sequencing device, and/or the electrode is positioned after the nanochannel, wherein one or more alignment structures is positioned in the nanochannel or also after the nanochannel. In any of these embodiments, and others described herein, the DNA sequencing device includes structures, fabrication methods, and/or operational features that assist in orienting and/or positioning a DNA strand 4 relative to one or more electrodes that are used to detect a tunneling current associated with individual nucleotides of a DNA strand.

Figure 3A:
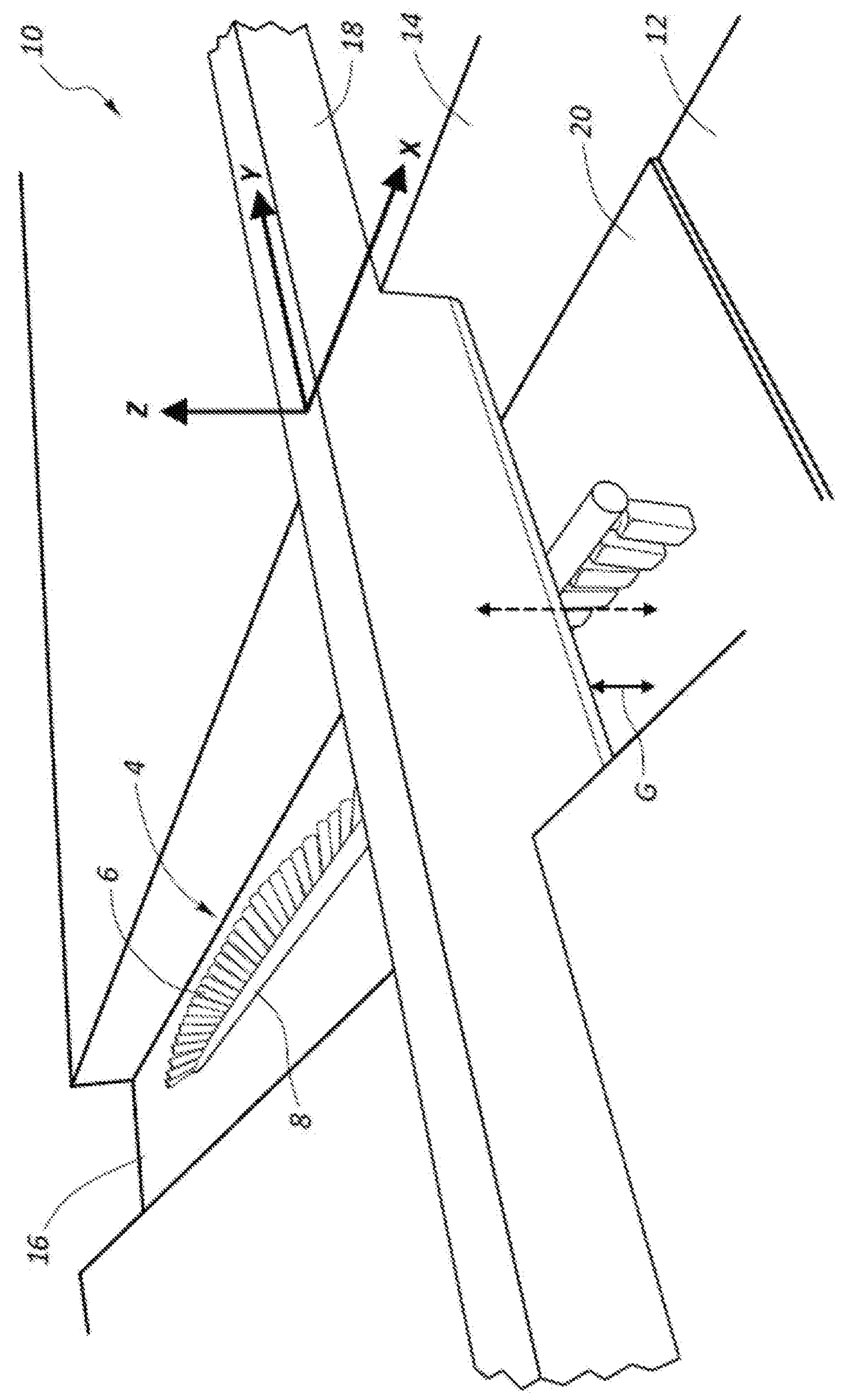
FIGS. 3A-3B show schematic perspective views of a portion of the DNA sequencing device of FIG. 2.
Figure 3B:
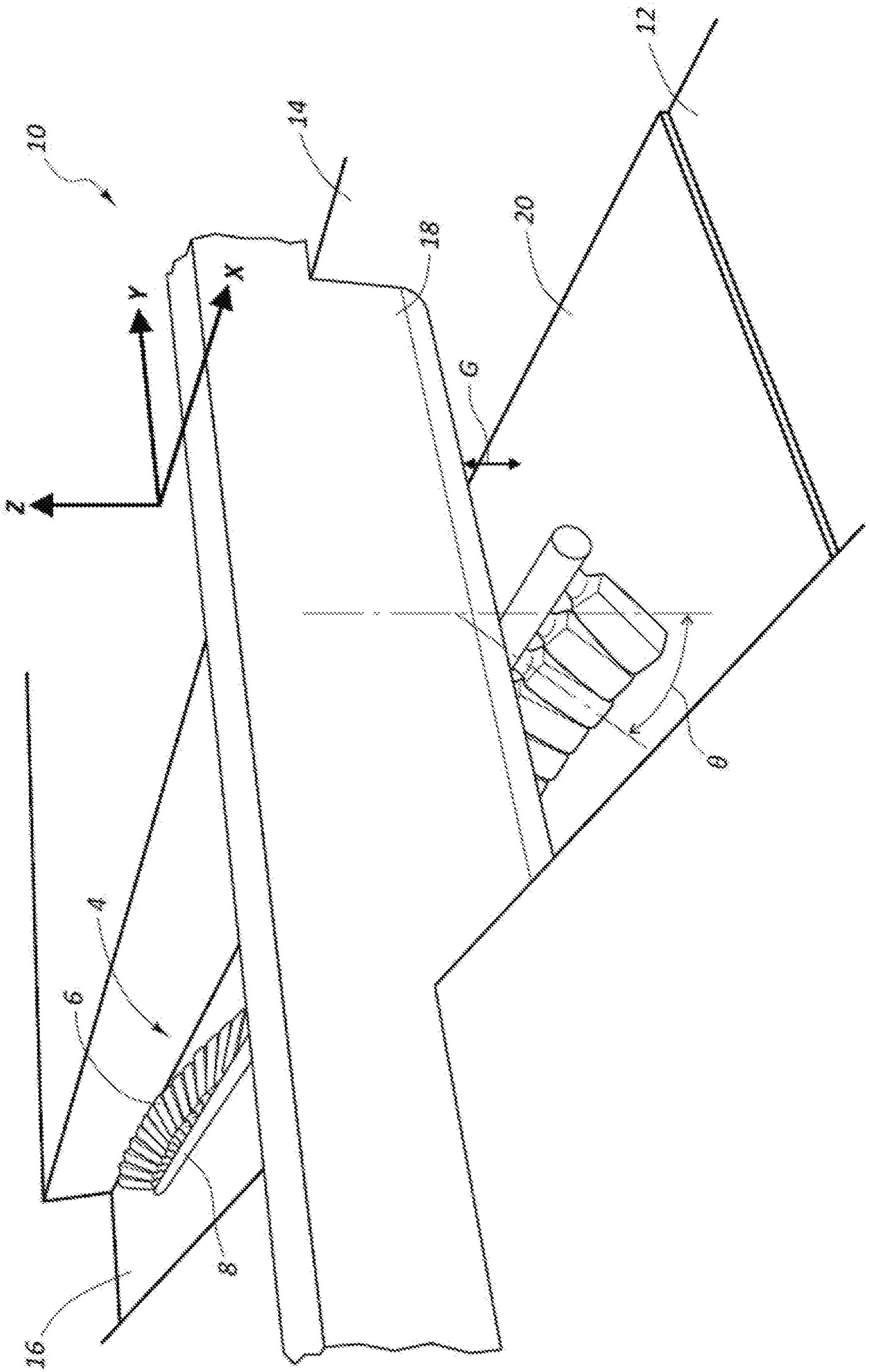

FIGS. 3A and 3B are perspective views showing a portion of the DNA sequencing device 10 with different nucleotide orientations relative to the electrode members 18, 20. FIG. 3A shows a first nucleotide orientation in the YZ plane. The orientation shown in FIG. 3A is similar to that shown in FIG. 2 in which the nucleotides 6 are oriented in alignment with the Z axis as the DNA strand 4 passes through the gap G. FIG. 3B shows a second nucleotide orientation in the YZ plane in which the nucleotides 6 are arranged at an angel θ relative to the Z axis. The two orientations shown in FIGS. 3A and 3B are examples of the many different orientations that are possible as the DNA strand 4 passes through the gap G between the electrode members 18, 20. Each orientation provides a different value for the tunneling current for the same nucleotide 6. Accordingly, one objective of the present disclosure is to provide a way for the nucleotides 6 to be oriented consistently in a given orientation as the DNA strand 4 passes through the gap G. This consistent orientation may improve discrimination between the nucleotide types (A,T,C,G).

A second issue that may be relevant to discriminating between nucleotides 6 is when the DNA strand 4 passes the electrode members 18, 20 at different points along the Y axis. The electrode members 18, 20 at the nanoscale dimensions involved in the DNA sequencing device 10 typically include some physical roughness that may lead to variations in the measured tunneling current if the DNA strand 4 does not pass through the gap G at a consistent location along the Y axis. Accordingly, another object to the present disclosure is to provide not only a consistent orientation for the nucleotides 6 within the gap G in the YZ plane, but also provide consistent positioning of the DNA strand 4 along the Y axis within the gap G as the DNA strand 4 passes through the gap G, and for each DNA strand 4 that is measured by the DNA sequencing device 10.

Figure 4:
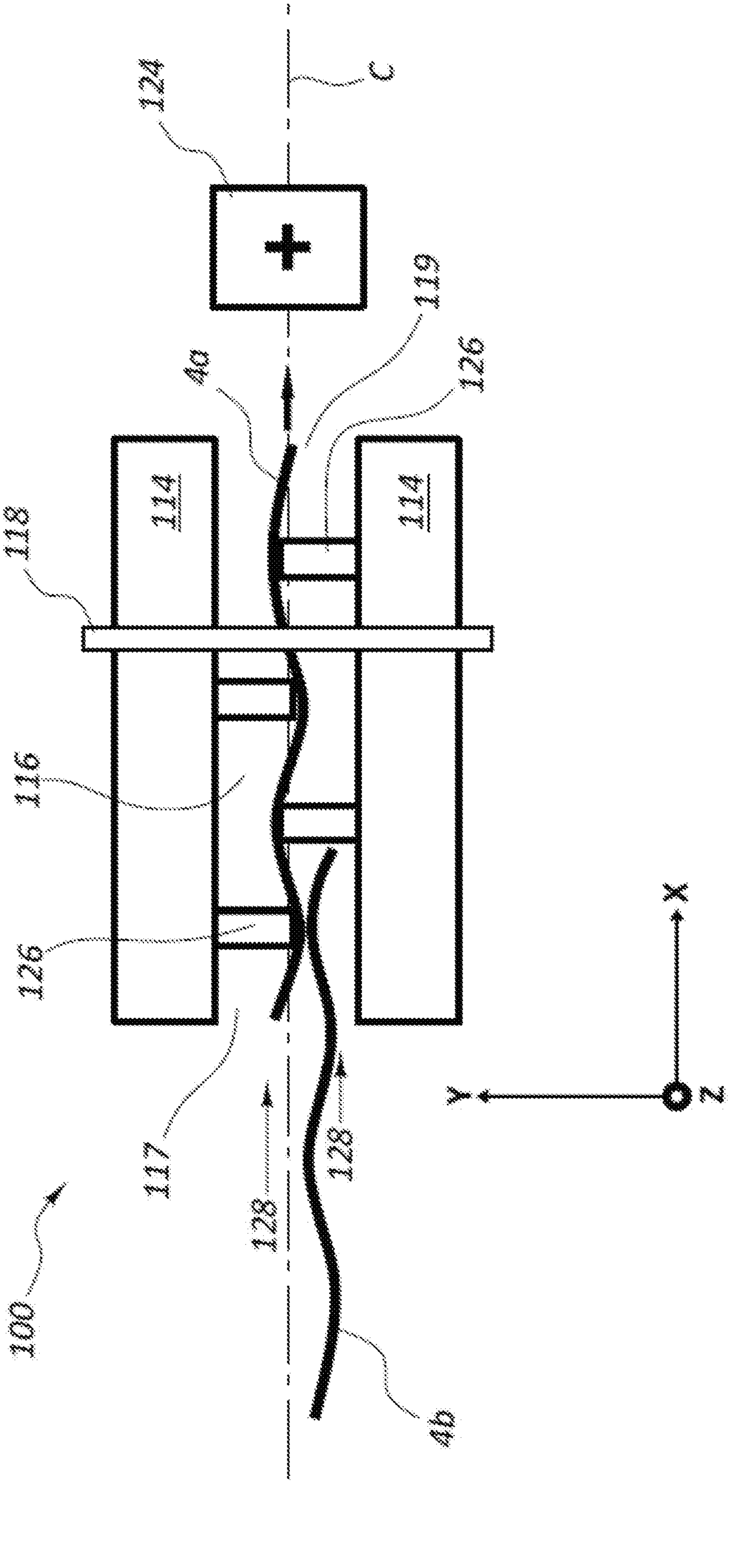
FIG. 4 shows a schematic top view of an example DNA sequencing device with alignment structures in accordance with the present disclosure.

FIG. 4 illustrates another example DNA sequencing device 100 as a schematic top view. The DNA sequencing device 100 includes an upper layer 114 (which is positioned on a substrate—not shown), a nanochannel 116 having inlet and outlet ends 117, 119, a first electrode member 118 (a second electrode member being positioned along the bottom surface of the nanochannel 116), and an energy source 124 that operates to draw the DNA strand through the nanochannel 116 using electrophoresis. The DNA sequencing device 100 also includes a plurality of alignment structures 126 positioned within the nanochannel 116. The alignment structures 126 may be offset from each other in a longitudinal direction along the length of the nanochannel 116. Alignment structures 126 may extend in the Y direction beyond a centerline C. The alignment structures 126 may have any desired shape and size. The alignment structures 126 shown in FIG. 4 have a generally rectangular cross-sectional shape. Other embodiments include, for example, hemispherical, circular, oval, triangular, and other shapes.

The basic physics involved with what is shown in FIG. 4 relate to tension of the DNA strand 4, which is already achieved by the pulling action of electrophoresis using the positive energy source 124. Each nucleotide 6 positioned along the DNA strand 4 possesses a negative charge. The lead nucleotide will sense a stronger pulling force towards the positive electrophoresis energy source 124 compared to the last nucleotide, once the DNA strand 4 is untangled prior to entering the nanochannel 16. FIG. 4 shows a first DNA strand 4A that is positioned within the nanochannel 116 and oriented extending around the alignment structures 126. A second DNA strand 4B is restricted from moving into the nanochannel 116 until after passage of the first DNA strand 4A through the nanochannel 116. The difference between the pulling force at the lead end versus the tail end of the DNA strand 4A within the nanochannel 116 produces a net tension on the DNA strand 4A. Further, the alignment structures 126 confine the DNA strand 4A due to tension as the DNA strand 4A passes the electrode member 118. As a result, the alignment structures 126 provide both consistent orientation and position confinement along the Y direction as the DNA strand 4 crosses the electrode member 118. The Y axis confinement along the one dimensional electrode member 118 may be helpful due to the atomic level roughness of the electrode member 118, which can influence the measured tunneling current if the particular nucleotide does not pass through the gap G between the electrode members in the same location along the Y axis. This Y axis confinement may be an important aspect of consistent, repeatable tunneling current measurements of the nucleotides 6.

An added benefit of using the alignment structures 126 is to enable DNA confinement, while providing intolerance to thin film processing variation. On such small nanometer scales, functional robustness to process tolerance may also be relevant. To enhance the tension of the DNA strand 4, additional alignment structures 126 may be added preceding the electrode member 118, thereby forming an asymmetric pattern of the alignment structures 126 with respect to the location of electrode member 118. As the DNA strand 4 is pulled through the electrode gap G, the additional resistance created by the increased number of alignment structures 126 may increase the physical contact area with the DNA strand 4. This greater amount of physical contact creates increased tension, which may ensure improved confinement at the DNA strand in the Y direction, as well as orientation of the nucleotides within the XY plane. Providing additional alignment structures 126 after the electrode member 118 may provide similar advantages, particularly for those nucleotides 6 further along the length of the DNA strand 4. In at least some arrangements, alignment structures may be positioned outside of the nanochannel 116 either preceding or following the inlet 117 and outlet 119 to provide similar advantages for orientation and positioning of the DNA strand 4 relative to the electrode member 118, electrode gap G and/or the nanochannel 116 generally.

Another potential benefit related to using alignment structures 126 is the ability to slow down the translation speed of the DNA strand 4 through the nanochannel 116. The added resistance provided by the alignment structures 126 may lead to a reduction in speed. As more alignment structures 126 are added preceding or following the electrode member 118, the speed can be reduced proportionally. Reducing the speed for the DNA strand 4 may provide improved measuring of the tunneling current at the electrode gap G.

The alignment structures 126 may also assist in limiting passage of only a single DNA strand 4 through the nanochannel 116 at a given time. Increasing or decreasing the number of alignment structures 126 may provide additional control of a number of DNA strands 4 that may be permitted to enter into and pass through the nanochannel 16 at a given time.

FIGS. 5A-5D show portions of additional DNA sequencing devices 200A-200D having different arrangements for the alignment structures 226 within a nanochannel 216. The alignment structures 226 have a circular cross-sectional shape, although any cross-sectional shape may be possible. Typically, any shape may be sufficient as long as the alignment structures 226 encroach past the centerline C between the two rows of alignment structures 226. This overlap beyond the centerline C in the Y direction may provide increased physical tension on the DNA strand 4 as it passes through the nanochannel 216.

Figure 5A:
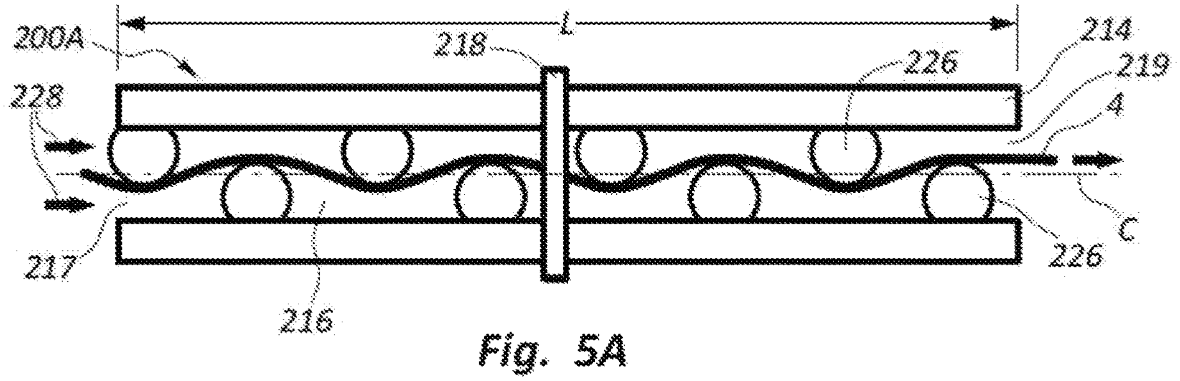
FIGS. 5A-5D show schematic top views of example DNA sequencing devices with various alignment structure arrangements in accordance with the present disclosure.

FIG. 5A shows a DNA sequencing device 200A that includes an upper layer 214, a nanochannel 216 having inlet and outlet ends 217, 219, a first electrode member 218 (a second electrode member typically being positioned opposite the first electrode member 218 along a bottom surface of the nanochannel 216), and a plurality of alignment structures 226 positioned in the nanochannel 216. The first electrode 218 is oriented perpendicular to the nanochannel 216. The electrode 218 is positioned in a gap between alignment structures 226, which are positioned on opposite sides of the nanochannel 216 as part of two separate rows 228 of alignment structures 226. The electrode member 218 is also positioned generally at a midpoint along the length of the nanochannel 216. The alignment structures 226 provide alignment and/or tension of a DNA strand 4 passing through the nanochannel 216 at locations before and after the electrode 218.

Figure 5B:
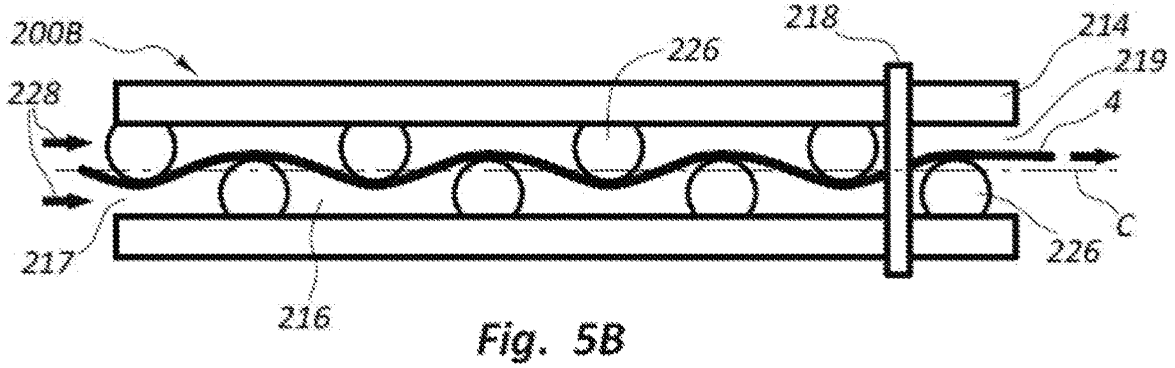

FIG. 5B shows a DNA sequencing device 200B that includes the electrode member 218 positioned spaced between alignment structures 226 of the separate rows 228. The electrode member 218 is also positioned near the outlet end 219 of the nanochannel 216. The DNA strand 4 passing through the nanochannel 216 has the benefit of being aligned and tensioned by all of the alignment structures 226 except the single alignment structure 226 positioned after or downstream of the electrode member 218.

Figure 5C:
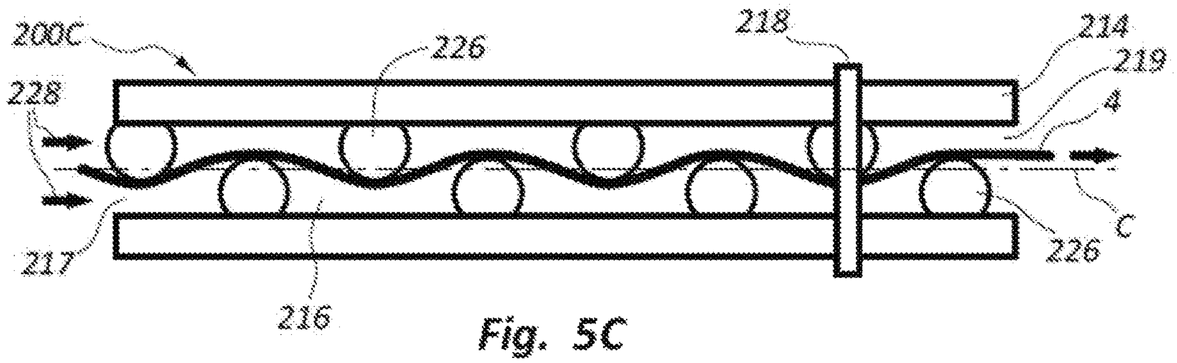

FIG. 5C shows a DNA sequencing device 200C in which the electrode member 218 overlaps with one of the alignment structures 226. The DNA strand 4 is in contact with the alignment structure 226 while also being positioned within the gap G between the electrode members. The physical contact between the DNA strand 4 and the alignment structure 226 may provide improved orientation and positioning of the DNA strand 4 relative to the electrode member 218 as well as positioning of the DNA strand 4 in the Y direction relative to the electrode member 218.

Figure 5D:
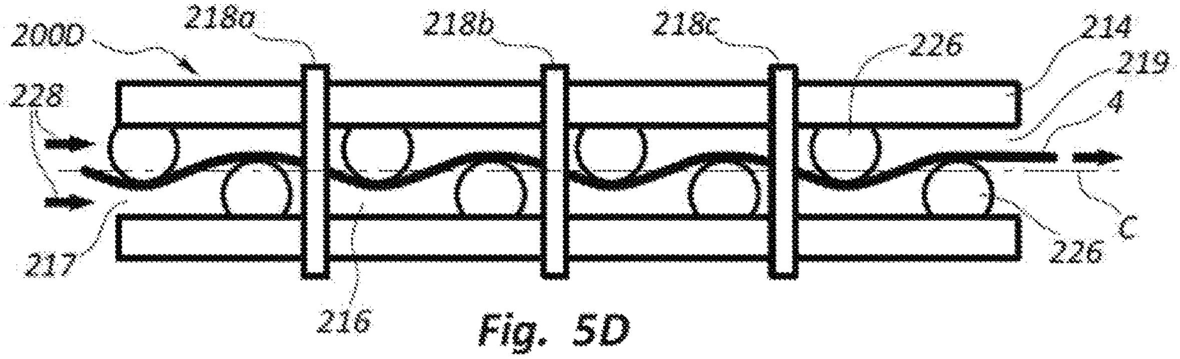

FIG. 5D shows a DNA sequencing device 200D that includes a plurality of electrode members 218A, 218B, 218C spaced along the length of the nanochannel 216. Each of the electrode members 218A-218C may be paired with a second electrode member that is positioned on an opposite side of the nanochannel 216 to define a separate gap G. Each of the electrodes 218A-218C may provide a separate tunneling current measurement for the nucleotides of the DNA strand 4. Providing multiple electrode pairs along the length of the nanochannel 216 may provide improved accuracy in measuring the tunneling current and detecting the sequence of the nucleotides positioned along the length of the DNA strand 4.

The electrode members 218A-218C are shown positioned between alignment structures 226 of the separate rows 228. In other embodiments, at least some of the electrode members 218A-218C may be positioned overlapping one or more of the alignment structures 226 (e.g., the arrangement shown in FIG. 5C). Further, one or more of the electrode members 218A-218C may be positioned outside of the nanochannel 216 to provide a tunneling current measurement of the DNA strand 4, for example, before entering or after exiting the nanochannel 216.

Figure 6:
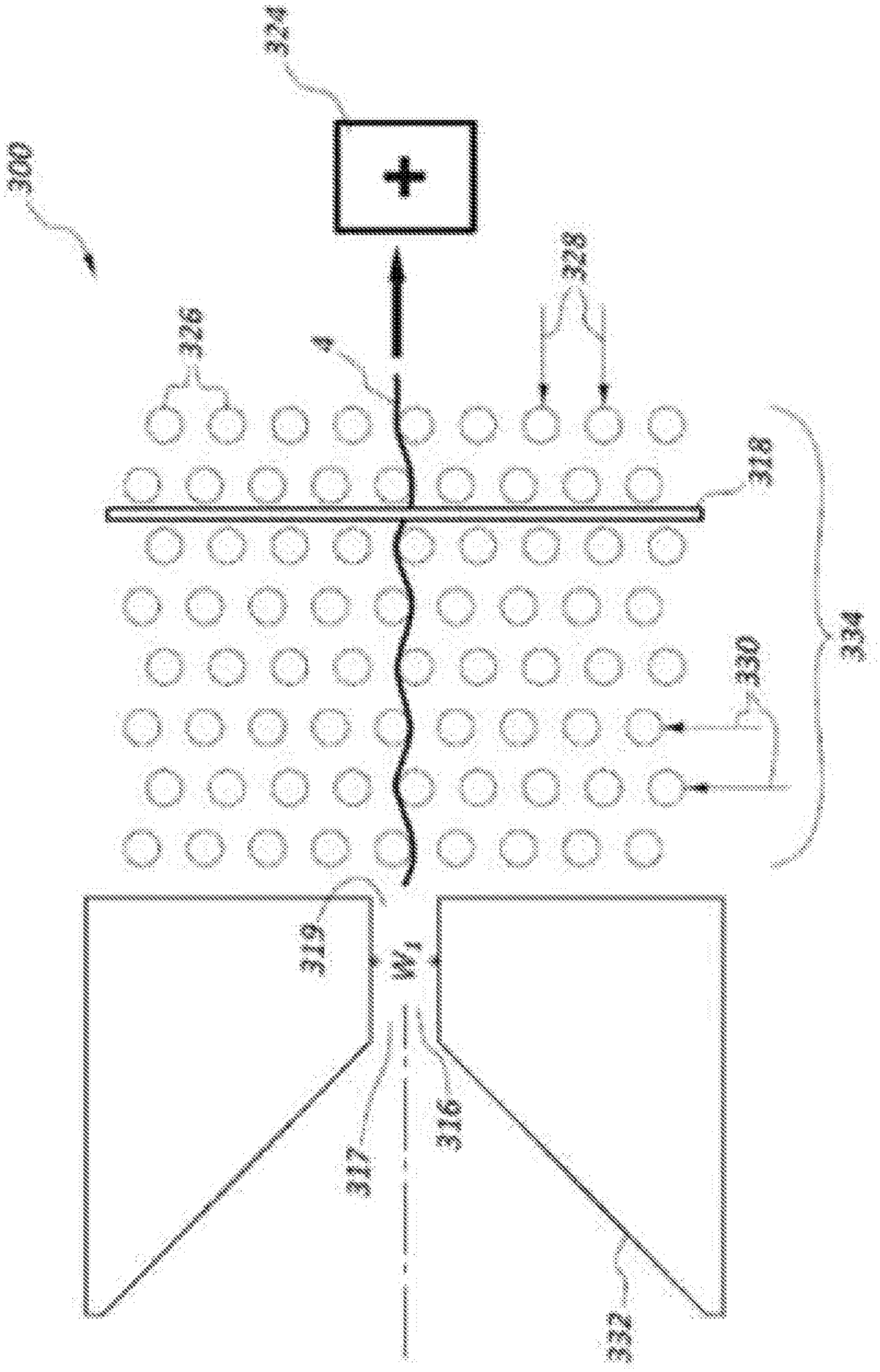
FIG. 6 shows a schematic top view of an example DNA sequencing device with alignment structures and an entry structure in accordance with the present disclosure.

Forming the alignment structures in a nanochannel may present fabrication challenges. FIG. 6 illustrates an alternative DNA sequencing device 300 that may provide a similar function as the embodiments discussed above (e.g., separation of DNA strands 4 while providing a consistent orientation and position relative to the electrode member as the DNA strand 4 translates toward the energy source as part of electrophoresis). FIG. 6 shows a funnel-shaped channel entry structure 332 that has a narrowing restriction in the form of a channel 316 with a width $W_1$. The channel 316 includes inlet and outlet ends 317, 319. The channel 316 may limit passage of a single DNA strand 4 to flow through the channel 316 at a time. The size of the channel 316 may be about 1 nm to as much as 100 nm, and is sized to limit, in conjunction with the funnel-shaped entry structure 332, a single DNA strand 4 to enter a field or region 334 of alignment structures 326, which follows the channel 316.

The alignment structures 326 are arranged in a plurality of rows 328 and columns 330. The alignment structure 326 in the rows 328 and columns 330 may be offset from each other to provide a tortuous path for the DNA strand 4 to pass through as the DNA strand 4 exits the channel 316 and moves toward the energy source 324. The electrode member 318 may be positioned in a gap between adjacent columns 330 of alignment structures 326. In other embodiments, the electrode member 318 may at least partially overlap at least some of the alignment structures 326 (e.g., within a given row 328 or column 330). The number of rows 328 and columns 330 may vary depending on a variety of factors. For example, the greater the number of rows 328, potentially the more likely the DNA strand 4 will remain within the region 334 prior to passing through the gap G associated with the electrode member 318. In another example, the greater the number of columns 330, potentially the greater the amount of tension and alignment provided to the DNA strand 4 to assist with consistent orientation and positioning of the DNA strand 4 relative to the electrode member 318.

Figure 7:
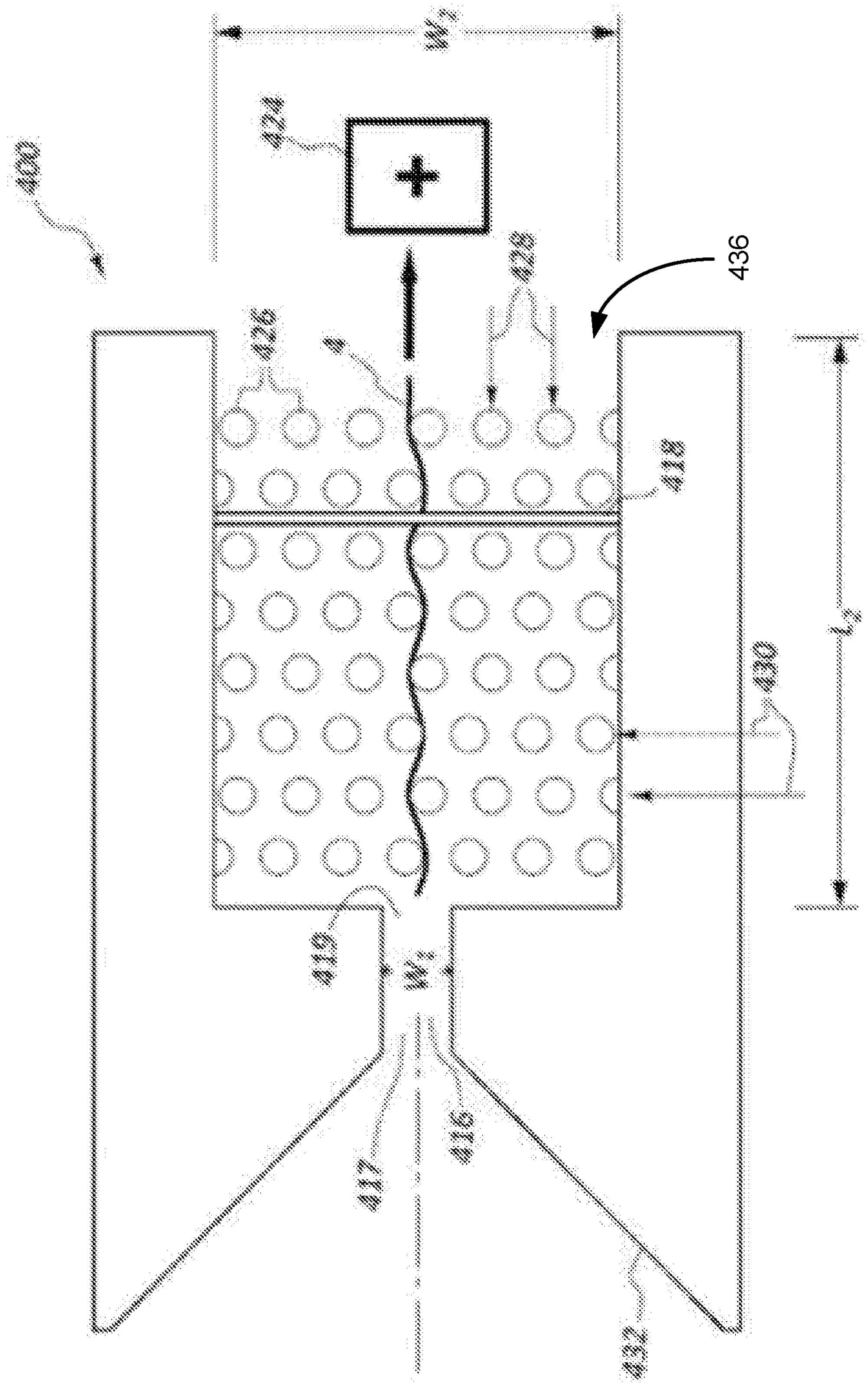
FIG. 7 shows a schematic top view of an example DNA sequencing device with alignment structures positioned in a main channel in accordance with the present disclosure.

FIG. 7 illustrates another example DNA sequencing device 400 that includes an entry structure 432 that is similar to the entry structure described with reference to FIG. 6, as well as a main channel 436 that follows a channel 416, which includes entry and exit ends 417, 419. The main channel 436 has a width W2, which may confine the alignment structures 426 within a limited space. The alignment structures 426 are arranged in rows 428 and columns 430, and are offset relative to each other. The arrangement of the alignment structures 426 may provide a tortuous path for a DNA strand 4 to pass through as it exits the channel 416, and moves towards the energy source 424 as part of electrophoresis. The number of rows 428 and columns 430 may influence the amount of tension and alignment imposed upon the DNA strand 4 as it moves through the electrode gap associated with the electrode member 418.

FIG. 7 illustrates a number of rows 428 and columns 430 of alignment structures 426 that provide a certain number of alignment structures in a given arrangement. Many other numbers of rows 428 and columns 430, as well as arrangements generally for the alignment structures 426 may be possible within a given main channel 436 having a width W2 and/or length L2. Furthermore, the electrode member 418 may be positioned at various locations along the length L2, or more than one electrode member (e.g., electrode pair with associated electrode gap G) may be used within a given main channel 436. In still further embodiments, separate electrode members 418 (or pairs of electrode members defining a gap G) may be positioned within channel 416 as well as within the main channel 436. In other embodiments, one or more alignment structures 426 may be positioned within the channel 416 as well as within the main channel 436, or even within the tapered portion of the entry structure 432 in the area prior to the entry 417 of the channel 416.

Figure 8:
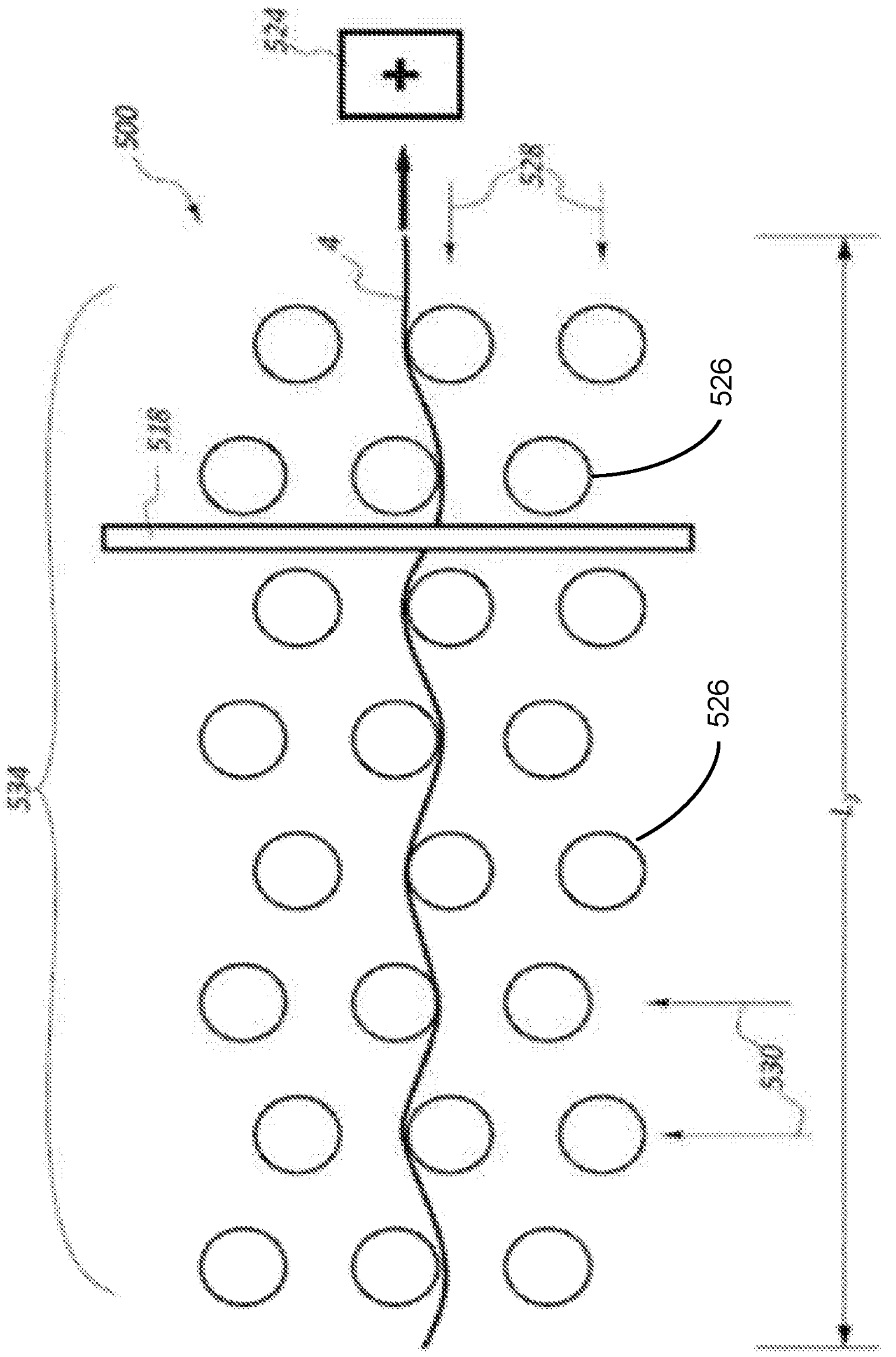
FIG. 8 shows a schematic top view of an example DNA sequencing device that is free of channel structures in accordance with the present disclosure.

FIG. 8 illustrates a DNA sequencing device 500 that includes a plurality of alignment structures 526 arranged in rows 528 and columns 530. The alignment structures 526 are arranged generally in a region 534 that is not confined by a channel structure. The direction of travel for a DNA strand 4 is dependent on, for example, electrophoresis created in part by positive power source 524 that draws the negatively charged DNA strand 4 through the region 534 of alignment structures 526. The electrode member 518 and associated electrode gap may be positioned at any location within the region 534. For example, the electrode member 518 is shown positioned between adjacent columns 530 of alignment structures 526 toward one end of the region 534. Other embodiments may provide positioning of the electrode member 518 at least partially overlapping at least some of the alignment structures 526, and/or positioned at various locations along a length L3 of the region 534.

The electrode member 518 and associated electrode gap may be positioned at any location within the region 534. For example, the electrode member 518 is shown positioned between adjacent columns 530 of alignment structures 526 toward one end of the region 534. Other embodiments may provide positioning of the electrode member 518 at least partially overlapping at least some of the alignment structures 526, and/or positioned at various locations along a length L3 of the region 534.

Figure 9A:
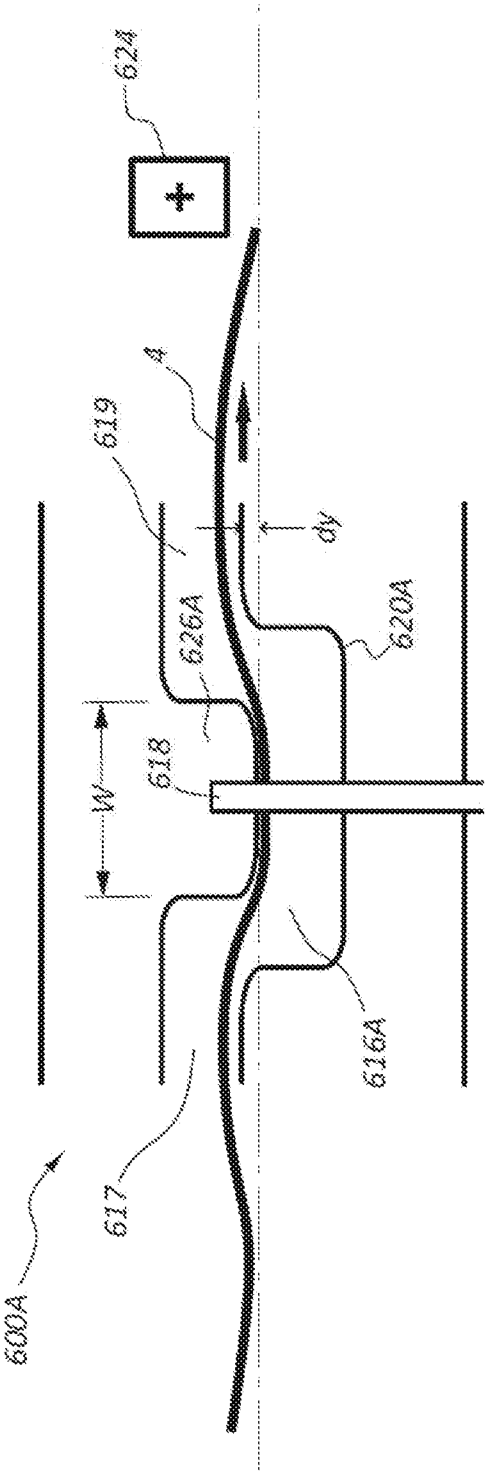
FIGS. 9A-9B show schematic top views of example DNA sequencing devices with alignment structures arranged opposite a divot or groove in a channel in accordance with the present disclosure.

FIG. 9A illustrates a DNA sequencing device 600A that includes an alignment structure 626A arranged in a channel 616A. The alignment structure 626A is arranged opposite a divot or groove 620A formed in the channel 616A. The resulting bend in the otherwise linear shape of the channel 616A may provide a contact point for the DNA strand 4 against the alignment structure 626A as the DNA strand 4 is drawn through the channel 616A by charge 624 using electrophoresis. The contact of DNA strand 4 with the alignment structure 626A may align the individual nucleotides of the DNA strand 4 in a consistent orientation relative to the electrode 618. This consistent orientation of the nucleotides may improve the consistency of detecting changes in the electronic signals using the electrode 618. The alignment structure 626A may have a width W measured in a direction along the length of the channel 616A. The alignment structure 626A may create a change in the pathway of the DNA strand 4 an amount shown by measurement $d_y$.

Figure 9B:
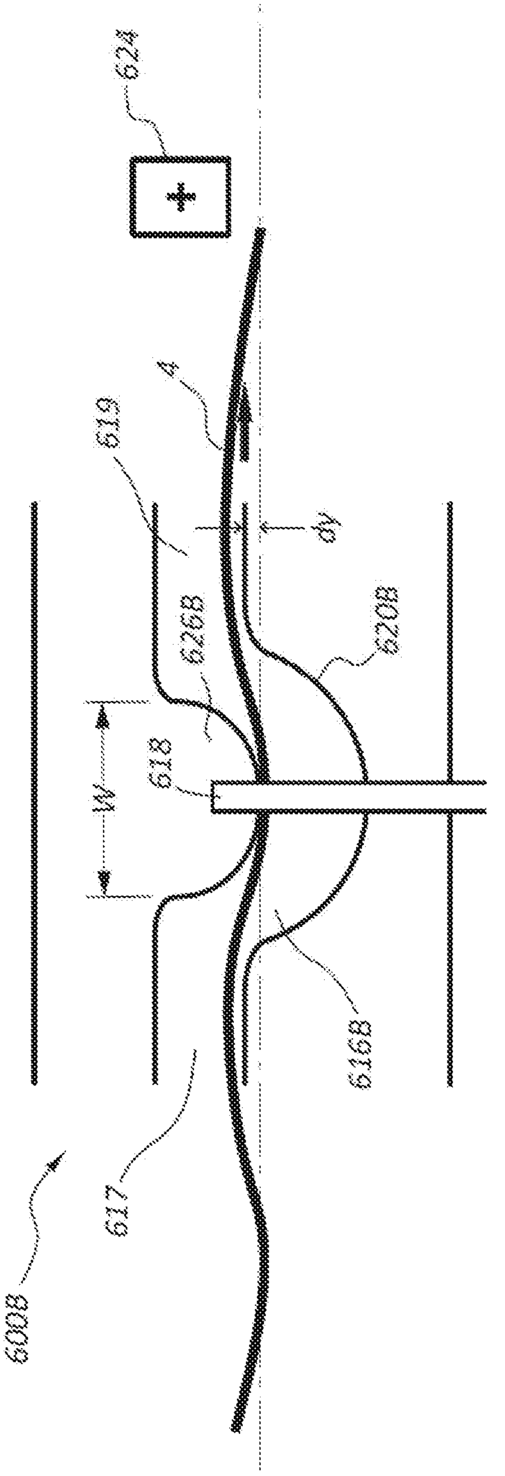

FIG. 9B illustrates a DNA sequencing device 600B that includes an alignment structure 626B arranged in a channel 616B. The alignment structure 626B is arranged opposite a divot or groove 620B formed in the channel 616B. The resulting bend in the otherwise linear shape of the channel 616B may provide a contact point for the DNA strand 4 against the alignment structure 626B as the DNA strand 4 is drawn through the channel 616B by charge 624 using electrophoresis. The contact of DNA strand 4 with the alignment structure 626B may align the individual nucleotides of the DNA strand 4 in a consistent orientation relative to the electrode 618. This consistent orientation of the nucleotides may improve the consistency of detecting changes in the electronic signals using the electrode 618. The alignment structure 626B may have a width W measured in a direction along the length of the channel 616B. The alignment structure 626B may create a change in the pathway of the DNA strand 4 an amount shown by measurement $d_y$.

The shape and size of the alignment structures 626A,B and grooves 620A,B may vary in different embodiments, and may provide for different $d_y$, different paths for the DNA strand 4, and different orientations for the nucleotides of the DNA strand 4. Furthermore, the alignment structures 626A,B and grooves 620A,B may be positioned at any desired location along the length of the channels 616A,B.

The spacing between the alignment structures in any of the embodiments disclosed herein is typically the maximum dimension (e.g., diameter in the case of the circular cross-sectional shaped alignment structures shown in FIGS. 5-8) plus an additional approximately 0.5 nm to about 2 nm, and more preferably about an additional 1 nm. In some embodiments, the spacing between the alignment structures may be as great as, for example, 3-5 times the maximum dimension (e.g., diameter) of the alignment structures. In some arrangements, the alignment structures may have different shapes or sizes for a given DNA sequencing device. The spacing between the alignment structures may be based at least in part on the initial size and/or the shape of the alignment structures.

During fabrication of the DNA sequencing devices disclosed herein, the nanochannel structures may be formed in a channel layer that is positioned on a substrate. The alignment structures may be formed directly on the substrate. In other embodiments, the alignment structures may be formed on a separate layer that is positioned between the substrate and the channel layer. In other embodiments, the alignment structures may be formed separately and mounted to the substrate or at other locations (e.g., within a nanochannel or at a location preceding or following an electrode member).

One fabrication method may include formation of a master template with a dot pattern using nanoimprint lithography method to make the final DNA sequencing device structure. The master may be made with a combination of, for example, e-beam lithography methods and/or a block copolymer (BCP) self-assembly that is a standard process used to fabricate storage media.

Generally, the electrode gap for the DNA sequencing devices disclosed herein is in the order of about 0.3 nm to about 5 nm, particularly in the range of about 0.3 nm to about 2 nm, and more particularly about 1 nm. The alignment structures may be separated from each other with a spacing on the order of about 5 nm to about 100 nm, and more particularly about 10 nm to about 30 nm.

The size and shape of the alignment structures disclosed herein may be limited to, for example, the size and shape of the structure within which the alignment structures are positioned. For example, a height, width, thickness, etc., dimension of the alignment structures may be limited to the height, width, and thickness dimensions of a nanochannel or other structure of the DNA sequencing device within which the alignment structures are positioned. The alignment structures may have various shapes and/or sizes within a given DNA sequencing device. For example, the alignment structures within a given row may have alternating shapes and/or sizes to provide the desired tortuous path for the DNA strand to pass through. At least some of the embodiments described above reference a centerline C through a channel structure, and the alignment structures are sized to extend from one side of the channel beyond the centerline C in a lateral direction. Other embodiments may be possible in which the alignment structures extend laterally beyond a different reference point as opposed to a centerline C of a channel. In yet other embodiments, the channel shape itself, absent any additional alignment structures, may provide the orientation and positioning of the DNA strand relative to the electrode members and/or electrode gap. For example, the nanochannel may have a tapered or funnel structure in at least one plane that assists with orienting of the nucleotides, and may have other features that provide positioning of the DNA strand (e.g., in a Y direction) relative to the electrode members.

Figure 10:
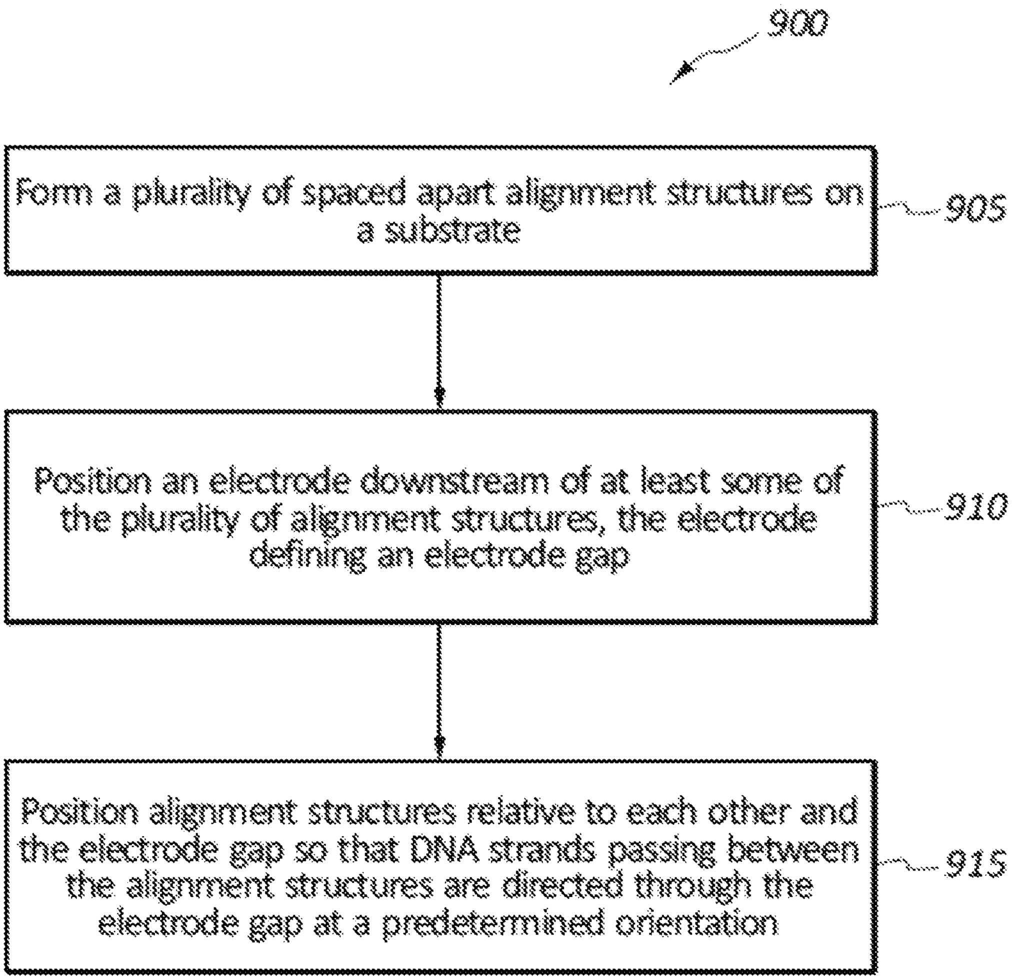
FIG. 10 is a flow diagram related to an example method in accordance with the present disclosure.
Figure 11:
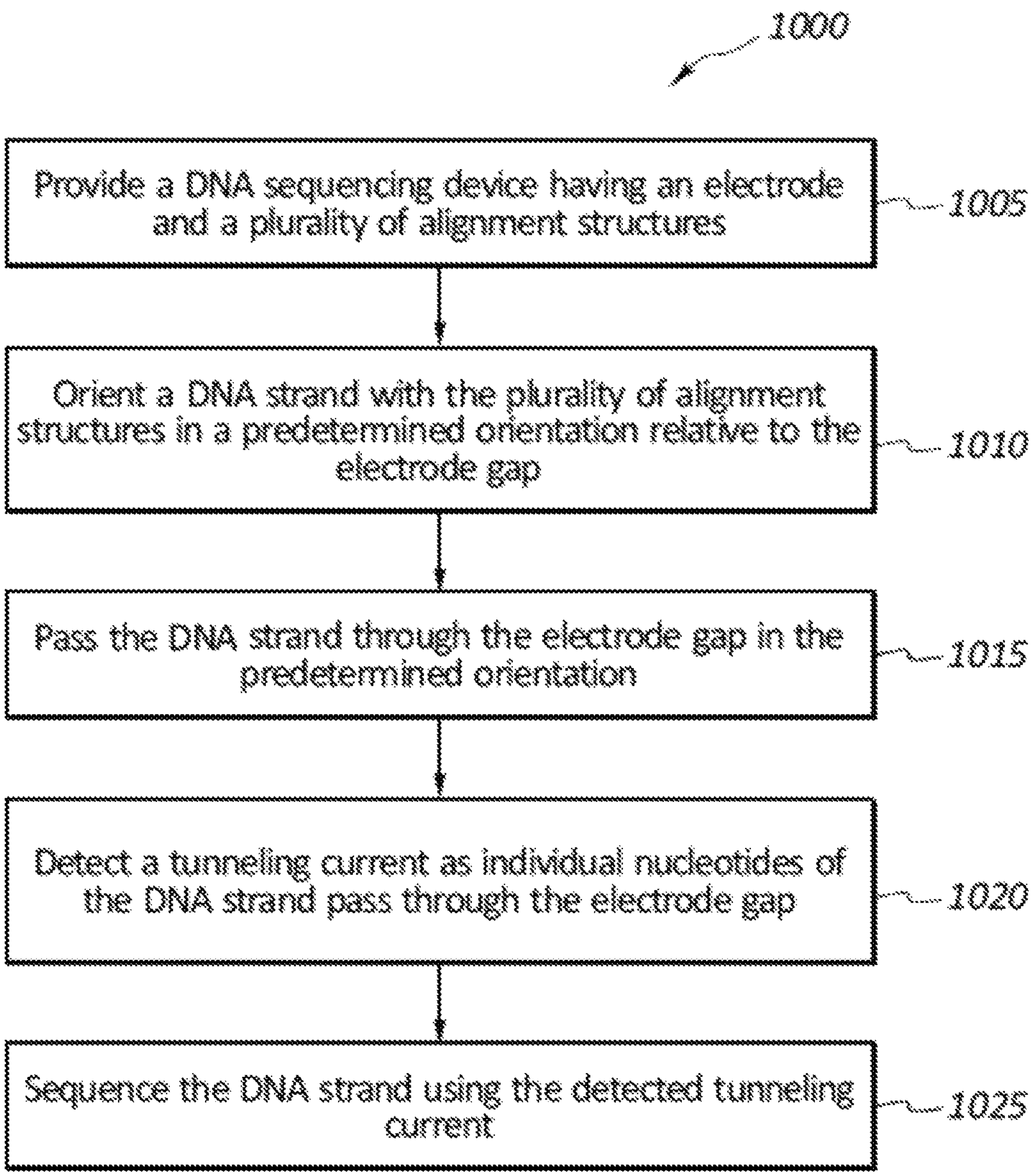
FIG. 11 is a flow diagram related to an example method in accordance with the present disclosure.

FIGS. 10 and 11 illustrate various methods related to the present disclosure. Some example methods are directed to manufacturing or fabrication methods for creating the DNA sequencing devices, or components thereof, as described herein. Other methods may relate to DNA sequencing using one or more of the DNA sequencing devices or related components.

FIG. 10 illustrates a method 900 for forming a DNA sequencing device. At block 905, the method may include forming a plurality of spaced apart alignment structures on a substrate. At block 910, the method may include positioning an electrode downstream of or after at least some of the plurality of alignment structures. The electrode may define an electrode gap. Block 915 includes positioning the alignment structures relative to each other and the electrode gap so that DNA strands and/or particular nucleotides of the DNA strands passing between the alignment structures are directed through the electrode gap a predetermined orientation and/or position. The method 900 may also include arranging at least some of the plurality alignment structures in rows with the alignment structures of one row being offset laterally and/or longitudinally from the alignment structures in an adjacent row. At least some of the alignment structures may be positioned downstream of or after the electrode gap. The method may include depositing a channel layer on the substrate, forming a nanochannel in the channel layer, and positioning at least some of the alignment structures inside the nanochannel. The method may include depositing a channel layer on the substrate, forming a nanochannel in the channel layer, and positioning at least some of the alignment structures outside of the nanochannel.

FIG. 11 illustrates a method 1000 related to DNA sequencing using, for example, the DNA sequencing devices disclosed herein, or components thereof. Block 1005 includes providing a DNA sequencing device having an electrode and a plurality of alignment structures. Block 1010 includes orienting a DNA strand with the plurality of alignment structures in a predetermined orientation or position relative to the electrode gap. The method 1000 includes passing the DNA strands through the electrode gap in the predetermined orientation at Block 1015. Block 1020 may include detecting a tunneling current as individual nucleotides of the DNA strand pass through the electrode gap. Block 1025 includes sequencing the DNA strand using the detected tunneling currents. The method may also include providing the DNA sequencing device with a nanochannel, and the electrode gap and at least some of the alignment structures are positioned in the nanochannel. The plurality of nanochannels may be arranged in rows with the alignment structures of one row being offset from the alignment structures in an adjacent row, at least some of the alignment structures being positioned upstream of or prior to the electrode, and at least some of the alignment structures being positioned downstream of or after the electrode.

The example methods 900, 1000 may, in other embodiments, include fewer or additional steps that those illustrated in FIGS. 10 and 11. Further, many other methods and method steps may be possible based on the disclosures provided herein.

Figure 12:
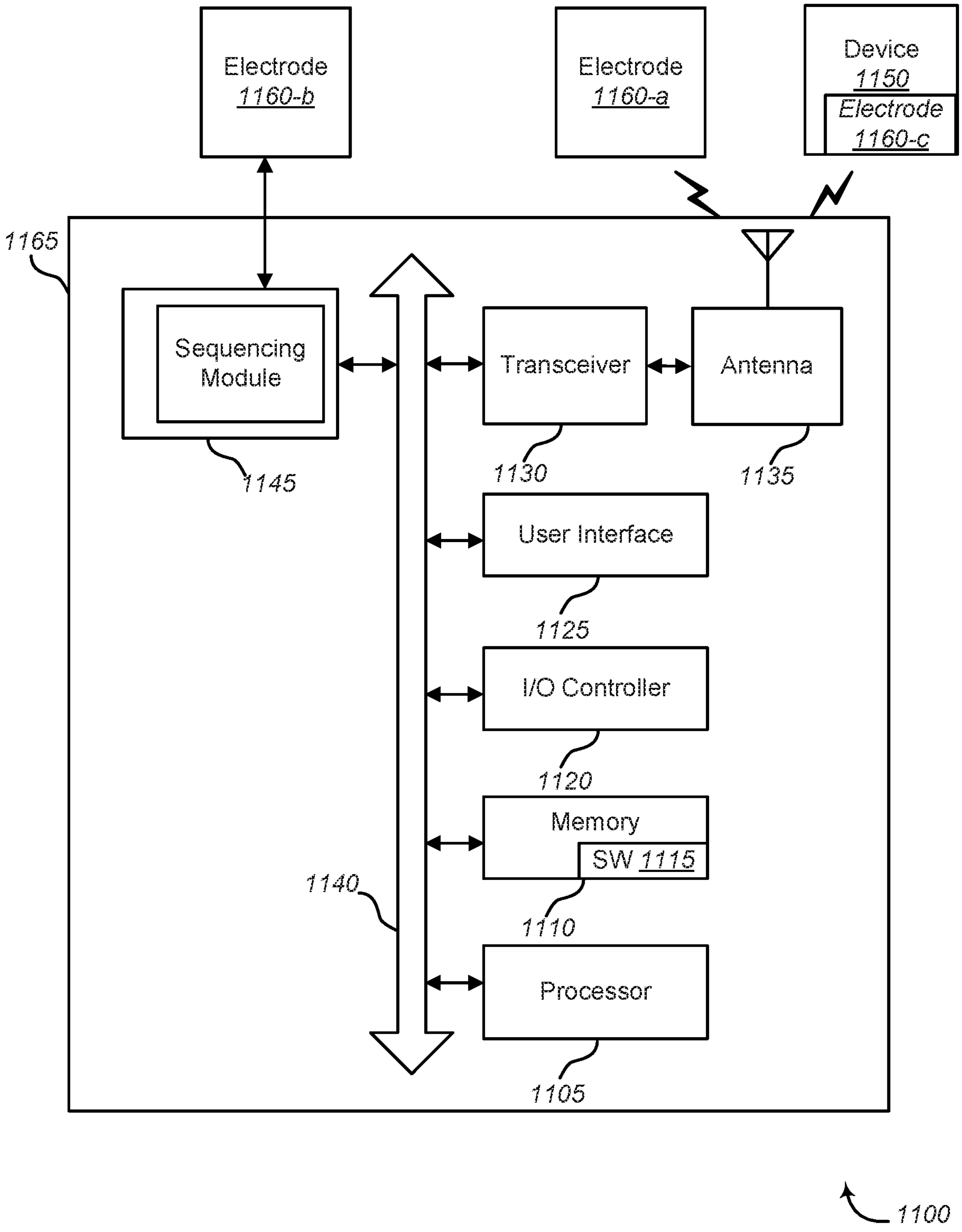
FIG. 12 shows a diagram of a system in accordance with various aspects of this disclosure.

FIG. 12 shows a system 1100 for use with the DNA sequencing devices and systems shown in FIGS. 1-8. System 1100 may include a control panel 1165. Control panel 1165 may be equivalent at least in part to a controller, control unit, processor or the like for use with the devices described above with reference to FIGS. 1-8. Control panel 1165 may include sequencing module 1145. The sequencing module 1145 may provide communications with one or more electrodes 1160 (also referred to as sensors or devices) directly or via other communication components, such as a transceiver 1130 and/or antenna 1135. The electrodes 1160 may represent one or more of the electrodes 18, 20, or pairs of such electrodes in any of the embodiments described above. The sequencing module 1145 may perform or control various operations associated with, for example, the electrodes 18, 20, actuators, controllers (e.g., controller 22), or other components of the DNA sequencing devices and related systems as described above with reference to FIGS. 1-7.

Control panel 1165 may also include a processor module 1105, and memory 1110 (including software/firmware code (SW) 1115), an input/output controller module 1120, a user interface module 1125, a transceiver module 1130, and one or more antennas 1135 each of which may communicate, directly or indirectly, with one another (e.g., via one or more buses 1140). The transceiver module 1130 may communicate bi-directionally, via the one or more antennas 1135, wired links, and/or wireless links, with one or more networks or remote devices. For example, the transceiver module 1130 may communicate bi-directionally with one or more of device 1150 and/or electrodes 1160-*a*, 1160-*c*. The device 1150 may be components of the DNA sequencing devices and related systems and devices described with reference to FIGS. 1-7, or other devices in communication with such systems and devices. The transceiver 1130 may include a modem to modulate the packets and provide the modulated packets to the one or more antennas 1135 for transmission, and to demodulate packets received from the one or more antennas 1135. In some embodiments (not shown) the transceiver may be communicate bi-directionally with one or more of device 1150, remote control device 1155, and/or electrodes 1160-*a*, 1160-*c* through a hardwired connection without necessarily using antenna 1135. While a control panel or a control device (e.g., 1105) may include a single antenna 1135, the control panel or the control device may also have multiple antennas 1135 capable of concurrently transmitting or receiving multiple wired and/or wireless transmissions. In some embodiments, one element of control panel 1165 (e.g., one or more antennas 1135, transceiver module 1130, etc.) may provide a connection using wireless techniques, including digital cellular telephone connection, Cellular Digital Packet Data (CDPD) connection, digital satellite data connection, and/or another connection.

The signals associated with system 1100 may include wireless communication signals such as radio frequency, electromagnetics, local area network (LAN), wide area network (WAN), virtual private network (VPN), wireless network (using 302.11, for example), 345 MHz, Z-WAVE® communication protocol, cellular network (using 3G and/or LTE, for example), and/or other signals. The one or more antennas 1135 and/or transceiver module 1130 may include or be related to, but are not limited to, WWAN (GSM, CDMA, and WCDMA), WLAN (including BLUETOOTH® connectivity standard and Wi-Fi), WMAN (WiMAX), antennas for mobile communications, antennas for Wireless Personal Area Network (WPAN) applications (including RFID and UWB). In some embodiments, each antenna 1135 may receive signals or information specific and/or exclusive to itself. In other embodiments, each antenna 1135 may receive signals or information not specific or exclusive to itself.

In some embodiments, one or more electrodes 1160 (e.g., voltage, inductance, resistance, current, force, temperature, etc.) or devices 1150 may connect to some element of system 1100 via a network using one or more wired and/or wireless connections. In some embodiments, the user interface module 1125 may include an audio device, such as an external speaker system, an external display device such as a display screen, and/or an input device (e.g., remote control device interfaced with the user interface module 1125 directly and/or through I/O controller module 1120).

One or more buses 1140 may allow data communication between one or more elements of control panel 1165 (e.g., processor module 1105, memory 1110, I/O controller module 1120, user interface module 1125, etc.).

The memory 1110 may include random access memory (RAM), read only memory (ROM), flash RAM, and/or other types. The memory 1110 may store computer-readable, computer-executable software/firmware code 1115 including instructions that, when executed, cause the processor module 1105 to perform various functions described in this disclosure (e.g., initiating an adjustment of a lighting system, etc.). Alternatively, the software/firmware code 1115 may not be directly executable by the processor module 1105 but may cause a computer (e.g., when compiled and executed) to perform functions described herein. Alternatively, the computer-readable, computer-executable software/firmware code 1115 may not be directly executable by the processor module 1105 but may be configured to cause a computer (e.g., when compiled and executed) to perform functions described herein. The processor module 1105 may include an intelligent hardware device, e.g., a central processing unit (CPU), a microcontroller, an application-specific integrated circuit (ASIC), etc.

In some embodiments, the memory 1110 can contain, among other things, the Basic Input-Output system (BIOS) which may control basic hardware and/or software operation such as the interaction with peripheral components or devices. For example, the sequencing module 1145, and other modules and operational components of the control panel 1165 used to implement the present systems and methods may be stored within the system memory 1110. Applications resident with system 1100 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 1130, one or more antennas 1135, etc.).

Many other devices and/or subsystems may be connected to one or may be included as one or more elements of system 1100. In some embodiments, all of the elements shown in FIG. 12 need not be present to practice the present systems and methods. The devices and subsystems can be interconnected in different ways from that shown in FIG. 12. In some embodiments, an aspect of some operation of a system, such as that shown in FIG. 12, may be readily known in the art and are not discussed in detail in this application. Code to implement the present disclosure can be stored in a non-transitory computer-readable medium such as one or more of system memory 1110 or other memory. The operating system provided on I/O controller module 1120 may be iOS®, ANDROID®, MS-DOS®, MS-WINDOWS®, OS/2®, UNIX®, LINUX®, or another known operating system.

The transceiver module 1130 may include a modem configured to modulate the packets and provide the modulated packets to the antennas 1135 for transmission and/or to demodulate packets received from the antennas 1135. While the control panel or control device (e.g., 1105) may include a single antenna 1135, the control panel or control device (e.g., 1105) may have multiple antennas 1135 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.

U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A DNA sequencing device, comprising:

a nanochannel having an axial centerline extending in an x-direction, and a first wall, a second wall opposite the first wall in a y-direction, and a bottom wall defining a longitudinal flow channel;

an electrode comprising first and second electrode members spaced apart in a z-direction to define an electrode gap measured in the z-direction across the axial centerline of the nanochannel, the electrode gap being in the range of about 0.3 nm to about 2 nm, the electrode being operable to detect a change in tunneling current as a DNA strand passes through the electrode gap; and a plurality of alignment structures extending from the first wall in the y-direction and from the second wall in the y-direction upstream of the electrode members, the plurality of alignment structures spaced apart along the x-direction of the nanochannel, do not connect the first wall and the second wall and arranged to position nucleotides of the DNA strand in a predetermined orientation as the DNA strand passes through the electrode gap, at least one of the alignment structures extending from the first wall beyond the axial centerline of the nanochannel and at least another of the alignment structures extending from the second wall beyond the wherein the y-direction is perpendicular to the x-direction and the z-direction is perpendicular to both the x-direction and the y-direction.

2. The DNA sequencing device of claim 1, further comprising additional alignment structures positioned downstream of the electrode members in the nanochannel.

3. The DNA sequencing device of claim 1, further comprising a tapered channel entry structure positioned at an entrance end of the nanochannel, the tapered channel entry structure permitting only a single DNA strand at a time to pass into the nanochannel.

4. The DNA sequencing device of claim 1, wherein at least some of the alignment structures have one of a hemispherical shape, a circular cross-sectional shape, and a rectangular cross-sectional shape.

5. The DNA sequencing device of claim 1, further comprising at least one additional electrode, each additional electrode defining an additional electrode gap.

6. The DNA sequencing device of claim 1, wherein the electrode gap is positioned in an open space between at least two of the alignment structures.

7. The DNA sequencing device of claim 1, wherein the electrode gap is positioned overlapping at least one of the alignment structures.

8. The DNA sequencing device of claim 1, wherein the alignment structures extending from the first wall are offset in the x-direction from the alignment structures extending from the second wall.

9. The DNA sequencing device of claim 1, wherein the wherein the alignment structures extending from the first wall alternate in the x-direction with the alignment structures extending from the second wall.

10. A method of sequencing DNA, comprising:

providing the DNA sequencing device of claim 1;

orienting a DNA strand with the plurality of alignment structures in a predetermined orientation upstream of the electrode gap;

passing the DNA strand through the electrode gap in the predetermined orientation;

detecting a tunneling current as individual nucleotides of the DNA strand pass through the electrode gap and;

sequencing the DNA strand using the detected tunneling current.

11. The method of claim 10, further comprising passing the DNA strand through a second plurality of alignment structures downstream of the electrode.

* * * * *

UNITED STATES PATENT AND TRADEMARK OFFICE

CERTIFICATE OF CORRECTION

PATENT NO. : 10,761,058 B2
APPLICATION NO. : 15/886608
DATED : September 1, 2020
INVENTOR(S) : Thomas Young Chang et al.

It is certified that error appears in the above-identified patent and that said Letters Patent is hereby corrected as shown below:

In the Claims

In Column 17, Line 13, Claim 1, delete "beyond the" and insert --beyond the axial centerline,--

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*